(12) United States Patent
Goulas et al.

(10) Patent No.: US 11,274,088 B2
(45) Date of Patent: Mar. 15, 2022

(54) SYNTHESIS OF OLEOFURANS

(71) Applicant: Oregon State University, Corvallis, OR (US)

(72) Inventors: Konstantinos Goulas, Corvallis, OR (US); Nicholas L. Gadinas, Corvallis, OR (US); Kyle B. Reem, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 17/210,196

(22) Filed: Mar. 23, 2021

(65) Prior Publication Data

US 2021/0300884 A1 Sep. 30, 2021

Related U.S. Application Data

(60) Provisional application No. 62/993,788, filed on Mar. 24, 2020.

(51) Int. Cl.
*C07D 307/36* (2006.01)
*C07D 307/42* (2006.01)
*C07D 307/46* (2006.01)

(52) U.S. Cl.
CPC ......... *C07D 307/36* (2013.01); *C07D 307/42* (2013.01); *C07D 307/46* (2013.01)

(58) Field of Classification Search
None
See application file for complete search history.

(56) References Cited

U.S. PATENT DOCUMENTS

2018/0327375 A1 11/2018 Krumm et al.

FOREIGN PATENT DOCUMENTS

WO WO 2019/118862 6/2019
WO WO 2020/014304 1/2020

OTHER PUBLICATIONS

Ji et al., "Probing direct carbon-carbon acylation of furans and long-chain acids over H-ZSM-5," *Applied Catalysis A, General* 577:107-112, Mar. 21, 2019.
Nguyen, "Mechanistic Insights into Multi-Functional Catalysts for Biomass Conversion to Bio-Diesel and Bio-Surfactant," Ph.D. Dissertation, Section 1.3.3, pp. 15-17 and Chapter 6, pp. 117-133, Fall 2018.
Park et al., "Tunable Oleo-Furan Surfactants by Acylation of Renewable Furans," *ACS Central Science* 2:820-821, 2016.

*Primary Examiner* — Samantha L Shterengarts
(74) *Attorney, Agent, or Firm* — Klarquist, Sparkman, LLP

(57) ABSTRACT

Disclosed herein is a method for making oleofuran compounds according to formula 3

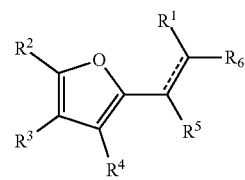

Formula 3 from a furan aldehyde or ketone and a fatty alcohol. The method comprises combining the furan compound and the fatty alcohol in the presence of a first catalyst to form an intermediate compound, and exposing the intermediate compound to hydrogen in the presence of a second catalyst to form the oleofuran compound. The hydrogen may be either hydrogen gas or hydrogen provided by a hydrogen donor.

20 Claims, No Drawings

SYNTHESIS OF OLEOFURANS

CROSS REFERENCE TO RELATED APPLICATION

This application claims the benefit of the earlier filing date of U.S. provisional patent application No. 62/993,788, filed on Mar. 24, 2020, which is incorporated herein by reference in its entirety.

FIELD

This disclosure concerns a method for making oleofuran compounds from an alcohol and a furan carbonyl compound.

BACKGROUND

Oleofuran sulfonate molecules are biomass-derived detergents with high performance in hard water. However, currently, the cost of oleofuran precursor production makes it difficult to develop a cost-competitive commercial oleofuran-based detergent. Current production methods require multiple steps for the production of the oleofuran precursor to the detergent molecule, often resulting in low overall yields. Additionally, many current methods rely on expensive and/or toxic reagents, such as trifluoroacetic acid anhydride, and/or produce a relatively large number of bi-products. This makes it difficult for oleofuran-based surfactants and/or detergents to compete with petrochemical-derived surfactants because of the increased cost associated with purchasing and disposing of reagents and/or bi-products.

SUMMARY

Disclosed herein is a method for making oleofurans that can be used as precursors for oleofuran-based surfactants, such as oleofuran sulfonates. Embodiments of the method minimize, or substantially exclude, using toxic and/or expensive reagents, and/or produce a small number of bi-products, thereby producing the oleofuran compounds with commercially useful the overall yields and at competitive costs. In some embodiments, the method comprises forming a first mixture comprising an alcohol, such as a fatty alcohol, and a compound according to formula 1 in the presence of a first catalyst

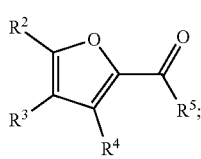

Formula 1 heating the first mixture at a first temperature of from 100° C. to 200° C. to form a compound according to formula 2

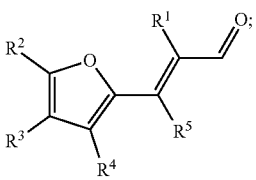

Formula 2 and
heating the compound according to formula 2 at a second temperature of from 120° C. to 220° C. in the presence of hydrogen and a second catalyst to form one or more compounds according to formula 3

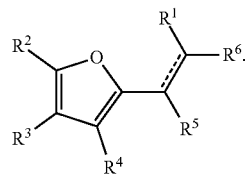

Formula 3

With respect to Formulas 1, 2 and 3, $R^1$ is aliphatic, typically alkyl, such as $C_{2-22}$alkyl or $C_{6-18}$alkyl. Each of $R^2$, $R^3$, and $R^4$ independently is H, aliphatic, aldehyde, or OH, such as H, alkyl, alkenyl, aldehyde, or OH, typically H or alkyl, such as H or $C_{1-6}$alkyl, and in some embodiments, at least $R^2$ and may be $R^2$, $R^3$ and $R^4$ are H. $R^5$ is H or alkyl, such as H or $C_{1-3}$alkyl, and in some embodiments, $R^5$ is H. $R^6$ is H, $CH_3$, or $CH_2OH$. And --- indicates that a bond may be a single bond or a double bond. And in some embodiments, the fatty alcohol has a formula

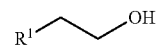

where $R^1$ is as defined herein for Formulas 1-3.

The first catalyst may be a basic catalyst and/or may comprise magnesium, such as magnesium oxide. In some embodiments, the first catalyst comprises a mixed oxide of magnesium and aluminum. In other embodiments, the first catalyst is or comprises a nickel catalyst. The nickel catalyst may be a Ni(II) catalyst, such as a homogeneous Ni(II) catalyst, for example, nickel (II) acetylacetonate, anhydrous $NiCl_2$, hydrous $NiCl_2$, or phosphine-ligated $Ni^{2+}$ catalysts, such as bis(triphenylphosphine)nickel(II) dichloride or bis(tricyclohexylphosphine)nickel(II) dichloride.

In some embodiments of the method, forming the first mixture comprises forming the first mixture in the presence of a base. The base may be an organic base, inorganic base, or a combination thereof. In certain embodiments, the base is an organic base such as pyrrolidine, or a trialkylamine, for example triethylamine or trimethylamine.

Heating the compound according to formula 2 in the presence of hydrogen may comprise heating the compound in the presence of hydrogen gas. However, in other embodiments, the compound is heated in the presence of a hydrogen donor. The hydrogen donor may be an alcohol, such as a secondary alcohol. A hydrogen donor alcohol may have a formula

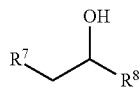

where each of $R^7$ and $R^8$ independently is H or alkyl. $R^7$ and $R^8$, together with the carbon atoms to which they are attached, may form a $C_{2-25}$ carbon chain. And in particular embodiments, $R^8$ is $CH_3$ and $R^7$ is H or $C_{1-18}$ alkyl, such as H or $C_{1-8}$ alkyl. Exemplary alcohols useful as hydrogen donors in the disclosed method include, but are not limited to, 2-propanol, 2-butanol, 2-pentanol, 2-hexanol, 2-heptanol or a combination thereof.

The second catalyst may be a metal oxide, a metallic catalyst, or a combination thereof. In some embodiments, the metal oxide comprises an oxide of Cu, Pd, Ru, Ir, Ti, Sn, Mo, Fe, In, W, Ni, Co, Zn, V or a combination thereof and/or the metallic catalyst comprises Re, Ni, Cu, Pd, Ru, Rh, Pt, Ag, Au, Ir, Zn or mixtures thereof. The metallic catalyst may further comprise a support substrate, such as carbon or a metal oxide, which may be the same metal oxide as is in the second catalyst, or a different metal oxide. In some embodiments, the second catalyst comprises the metallic catalyst supported on the metal oxide. In some embodiments, a portion of the metal oxide may be a film on top of a metallic substrate. In certain embodiments, the second catalyst is, or comprises, Ru/C, $RuO_2 \cdot H_2O$, $In_2O_3$, or a combination thereof.

In a particular embodiment, the method comprises forming a first mixture comprising an alcohol having a formula

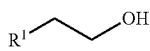

and a compound according to formula 1 in the presence of a first catalyst comprising magnesium and aluminum oxides

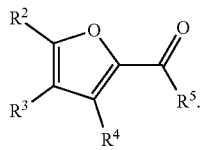

Formula 1

The first mixture is then heated at a first temperature of from 130° C. to 170° C. to form a compound according to formula 2

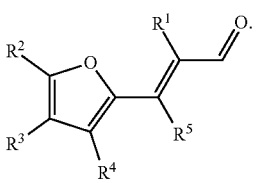

Formula 2

The compound according to formula 2 is then heated at a second temperature of from 150° C. to 200° C. in the presence of a secondary alcohol having a formula

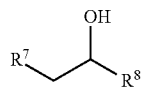

and a second catalyst comprising a metallic catalyst and a metal oxide to form one or more compounds according to formula 3

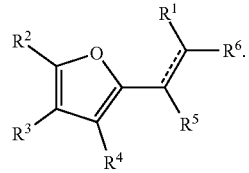

Formula 3

In some embodiments, $R^1$, $R^2$, $R^3$, $R^4$, $R^5$, $R^6$, $R^7$ and $R^8$ are as previously defined. And in certain embodiments, $R^1$ is $C_{2-22}$alkyl; each of $R^2$, $R^3$, and $R^4$ independently is H or $C_{1-6}$alkyl; $R^5$ is H; $R^6$ is H, $CH_3$, or $CH_2OH$; $R^7$ is H or $C_{1-18}$ alkyl; and $R^8$ is $CH_3$.

And in any embodiments, the one or more compounds according to formula 3 may be selected from

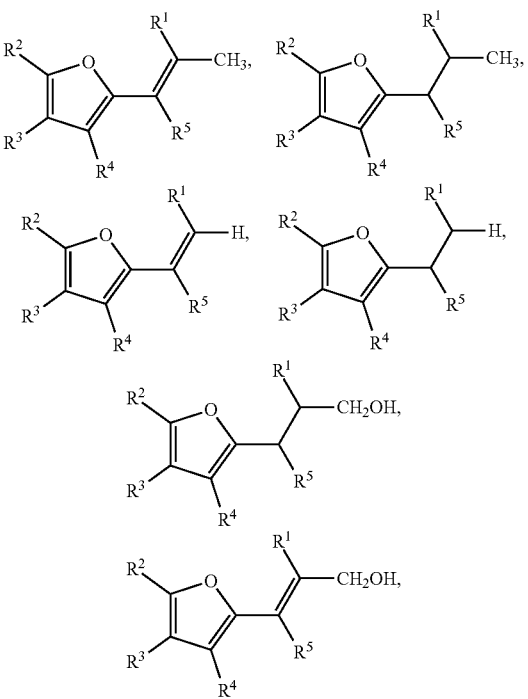

or a combination thereof.

The foregoing and other objects, features, and advantages of the invention will become more apparent from the following detailed description.

DETAILED DESCRIPTION

I. Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference in their entirety, unless otherwise specified.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that may depend on the desired properties sought and/or limits of detection under standard test conditions/ methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include implicit hydrogens such that each carbon conforms to a valence of four. For example, in the structure on the left-hand side of the schematic below there are nine hydrogen atoms implied. The nine hydrogen atoms are depicted in the right-hand structure.

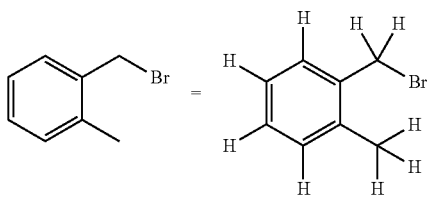

Sometimes a particular atom in a structure is described in textual formula as having a hydrogen or hydrogen atoms, for example —CH$_2$CH$_2$—. It will be understood by a person of ordinary skill in the art that the aforementioned descriptive techniques are common in the chemical arts to provide brevity and simplicity to description of organic structures.

In any embodiments, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl may be C$_2$H$_5$ or C$_2$H$_5$ where from 1 to 5 hydrogens are replaced by deuterium, such as in C$_2$D$_x$H$_{5-x}$.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diastereomers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms.

"Aldehyde" refers to the moiety —CHO, which also may be shown as —C(=O)H.

"Aliphatic" refers to a substantially hydrocarbon-based group or moiety. An aliphatic group or moiety can be acyclic, including alkyl, alkenyl, or alkynyl groups, cyclic versions thereof, such as cycloaliphatic groups or moieties including cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms (C$_{1-25}$); for example, from one to fifteen (C$_{1-15}$), from one to ten (C$_{1-10}$), from one to six (C$_{1-6}$), from one to four carbon atoms (C$_{1-4}$) or two to twenty two (C$_{2-22}$) or 6 to 18 (C$_{6-18}$) for a saturated acyclic aliphatic group or moiety, from two to twenty-five carbon atoms (C$_{2-25}$); for example, from two to fifteen (C$_{2-15}$), from two to ten (C$_{2-10}$), from two to six (C$_{2-6}$), or from two to four carbon atoms (C$_{2-4}$) for an unsaturated acyclic aliphatic group or moiety, or from three to fifteen (C$_{3-15}$) from three to ten (C$_{3-10}$), from three to six (C$_{3-6}$), or from three to four (C$_{3-4}$) carbon atoms for a cycloaliphatic group or moiety. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group). Substituents on an aliphatic group or moiety may be any substituents understood by a person of ordinary skill in the art to be compatible with the synthesis of the oleofuran compounds. Exemplary substituents include, but are not limited to, hydroxyl, amine, carbonyl (=O), aldehyde, or aliphatic, such as alkyl, alkenyl, alkynyl, and cyclic and branched versions thereof, preferably hydroxyl, aldehyde, or aliphatic, such as alkyl, alkenyl, alkynyl, and cyclic and branched versions thereof.

"Alkyl" refers to a saturated aliphatic hydrocarbyl group having from 1 to 25 (C$_{1-25}$) or more carbon atoms, such as from 1 to 10 (C$_{1-10}$) carbon atoms, from 1 to 6 (C$_{1-6}$) carbon atoms, or from 2 to 22 (C$_{2-22}$) carbon atoms or from 6 to 18 (C$_{6-18}$) carbon atoms. An alkyl moiety may be substituted or unsubstituted. This term includes, by way of example, linear and branched hydrocarbyl groups such as methyl (CH$_3$), ethyl (—CH$_2$CH$_3$), n-propyl (—CH$_2$CH$_2$CH$_3$), isopropyl (—CH(CH$_3$)$_2$), n-butyl (—CH$_2$—CH$_2$CH$_2$CH$_3$), isobutyl (—CH$_2$CH$_2$(CH$_3$)$_2$), sec-butyl (—CH(CH$_3$)(CH$_2$CH$_3$), t-butyl (—C(CH$_3$)$_3$), n-pentyl (—CH$_2$CH$_2$CH$_2$CH$_2$CH$_3$), neopentyl (—CH$_2$C(CH$_3$)$_3$), hexyl (C$_6$H$_{13}$), heptyl (C$_7$H$_{15}$), octyl (C$_8$H$_{17}$), decyl (C$_{10}$H$_{21}$), dodecyl (C$_{12}$H$_{25}$), tetradecyl (C$_{14}$H$_{29}$), hexadecyl (C$_{16}$H$_{33}$), octadecyl (C$_{18}$H$_{37}$) or eicosanyl (C$_{20}$H$_{41}$).

"Fatty alcohol" refers to an aliphatic alcohol compound having at least 4 carbon atoms in the aliphatic chain, such as from 4 to 30 carbon atoms or more, such as from 4 to 30, from 4 to 24, from 4 to 20, or from 8 to 20. Unless otherwise specified, the carbon chain in a fatty alcohol may be a straight chain, or it may be branched, cyclic, or a combination thereof.

"Hydroxyl" refers to a —OH moiety.

As used herein, the term "$C_{1-25}$ alcohol" and the like, refers to an alcohol, typically an aliphatic alcohol that comprises from 1 to 25 carbon atoms in addition to at least one OH moiety.

As used herein, a "hydrogen donor" is a compound that donates one or more hydrogens to another compound during a chemical reaction. For example, an alcohol may be a hydrogen donor if hydrogen is transferred from the alcohol to another compound during a chemical reaction and the alcohol forms a carbonyl moiety in place of the hydroxyl.

II. Method for Making Oleofuran Compounds

Disclosed herein is a method for making oleofuran compounds from an alcohol, such as a fatty alcohol, and a furan carbonyl compound, such as a furan aldehyde or ketone. Oleofuran compounds made by the disclosed method are useful as precursors for making oleofuran sulfonate compounds, such as oleofuran sulfonate detergents. The disclosed method may comprise two steps that may be performed in a single pot or in separate reactors. A person of ordinary skill in the art understands that if the reaction is performed in a single pot, the second catalyst may be added part way through the reaction, so that the aldehyde or ketone is not reduced by the catalyst too early in the reaction progression.

I. Step 1

The first step of the process is a tandem dehydrogenation and aldol condensation reaction, as shown in Scheme 1.

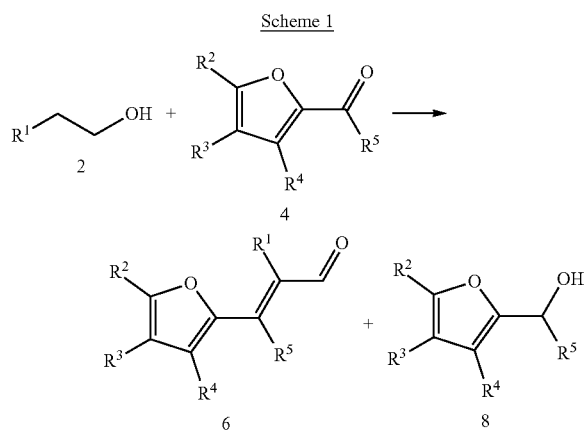

Scheme 1

With respect to Scheme 1, compound 2 is a fatty alcohol where $R^1$ is aliphatic, such as alkyl, alkenyl, or alkynyl, typically alkyl, such as $C_{2-22}$alkyl or $C_{6-18}$alkyl. Each of $R^2$, $R^3$, and $R^4$ independently is H, aliphatic, aldehyde, or OH, such as H, alkyl, alkenyl, aldehyde, or OH, and in certain embodiments, each of $R^2$, $R^3$, and $R^4$ independently is H or alkyl, such as H or $C_{1-6}$alkyl. In some embodiments, $R^2$ is H, and in certain embodiments, 2 of $R^2$, $R^3$ and $R^4$ is H, or $R^2$, $R^3$, and $R^4$ are all H. And $R^5$ is H or alkyl, such as H or $C_{1-6}$alkyl, or H or $C_{1-3}$alkyl, typically H or methyl, and in some embodiments, $R^5$ is H. In a particular embodiment, $R^2$, $R^3$, $R^4$ and $R^5$ are all H. Additionally, a person of ordinary skill in the art understands that there are various possible stereoisomers of compound 6 that are contemplated by the disclosure. For example, Scheme 1 shows the cis isomer of compound 6 with respect to $R^1$ and the furan ring about the double bond as an example structure. However, compound 6 also may exist as the trans isomer with respect to the furan ring and $R^1$, or compound 6 may comprise a mixture of cis and trans isomers, and both options are contemplated.

The reaction proceeds with a stoichiometric ratio of 2:1 aldehyde or ketone to fatty alcohol. That is, in the reaction, 2 equivalents of aldehyde or ketone are used per 1 equivalent of fatty alcohol, and one equivalent of aldehyde or ketone is converted to alcohol 8 during the reaction (Scheme 1). Accordingly, in some embodiments, aldehyde or ketone 4 and fatty alcohol 2 are in a molar ratio of 2:1. However, in other embodiments, the molar ratio of aldehyde or ketone 4 to fatty alcohol 2 is from 0.5:1 (i.e., excess alcohol) to 5:1 (i.e., excess furan compound) is used in the reaction.

The reaction may be performed in the presence of a catalyst. Suitable catalysts include any catalyst that facilitates the reaction in step 1. In some embodiments, the catalyst is a basic catalyst, such as a metal oxide catalyst, for example a magnesium oxide catalyst, or the catalyst may be a mixed metal oxide catalyst, for example, comprising both Mg and Al, such as hydrotalcite-derived mixed oxide comprising an Mg:Al ratio of 3:1, or $TiO_2$, $CeO_2$, $ZrO_2$, CaO, BaO, SrO, $Al_2O_3$, $SiO_2$, hydrotalcites, hydroxyapatites, amine-functionalized silica or any combination thereof.

In other embodiments, the catalyst may be a nickel catalyst, such as a Ni(II) catalyst. The nickel catalyst may be a homogeneous Ni catalyst, such as a homogeneous Ni(II) catalyst, for example, nickel (II) acetylacetonate, anhydrous $NiCl_2$, hydrous $NiCl_2$, or phosphine-ligated $Ni^{2+}$ catalysts. The Ni catalyst may be use in combination with a base, such as an organic base, inorganic base, or a combination thereof. Suitable bases include, but are not limited to, an amine, such as triethylamine, pyrrolidine or diisopropylethylamine; a carbonate, such as potassium carbonate or sodium carbonate, heterogeneous bases, such as amine-functionalized silica or any of the oxides mentioned in the previous paragraph; or a combination thereof.

In any embodiments, the reaction may be performed in a solvent suitable to facilitate the reaction, such as a aprotic solvent, for example, but without limitation, toluene, xylene, or an alkane, including branched and cycloalkanes, such as cyclohexane, cycloheptane, cyclooctane, n-heptane, n-octane, or a combination thereof. In embodiments where the reaction proceeds in the presence of an organic base, such as a trialkylamine, the organic base also may be used as the solvent. For example, triethylamine or diisopropylethylamine may be used as both the base and a solvent, or just as a base or just as a solvent. Additionally, or alternatively, the reaction may be performed in an excess of the fatty alcohol such that the excess fatty alcohol acts as a reaction solvent.

The reaction proceeds at a temperature suitable to facilitate compound 6 formation. In some embodiments, the reaction is performed at a temperature of from 100° C. or less to 200° C. or more, such as from 100° C. to 200° C., or from 130° C. to 170° C. Additionally, or alternatively, the reaction may proceed at a suitable pressure, such as an ambient pressure or an autogenous pressure where the reaction proceeds in a sealed reaction vessel and the pressure increases inside the vessel as the reaction temperature increases. The reaction may be heated for from greater than zero to 48 hours or more, such as from 1 hour to 48 hours, from 6 hours to 42 hours, from 12 hours to 36 hours, or from 18 hours to 24 hours.

After heating, the reaction mixture may be used without purification, or the catalyst may be removed by any suitable technique, such as filtration or decanting. The resulting liquid phase may be used without further purification, or compound 6 may be partially or fully isolated from the liquid phase. In some embodiments, the liquid phase is treated to increase the concentration of compound 6 in the liquid phase, such as by distilling off at least a portion of the solvent, unreacted starting materials, and/or unwanted reaction products such as compound 8.

II. Step 2

The second step of the synthesis is a hydrodeoxygenation reaction as shown in Scheme 2.

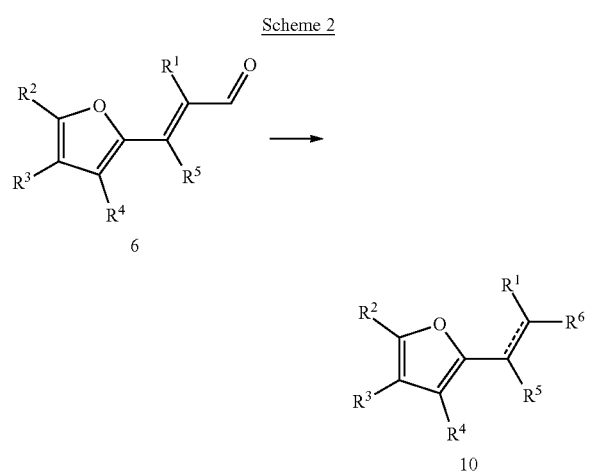

With respect to Scheme 2, $R^1$-$R^5$ are as defined in Scheme 1, $R^6$ is H, $CH_3$ or $CH_2OH$, and ═ indicates that the bond may be either a single or a double bond. Accordingly, compound 10 may be a single compound or a mixture of compounds, such as a mixture of 2, 3, 4, 5, or 6 compounds shown by formulas 10-a, 10-b, 10-c, 10-d, 10-e, and 10-f below:

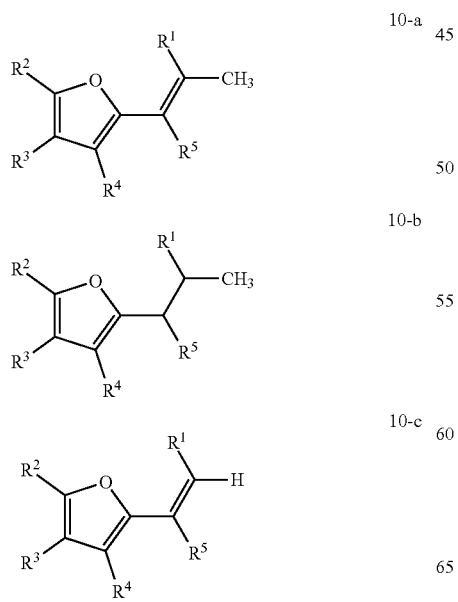

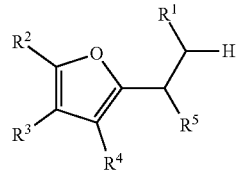

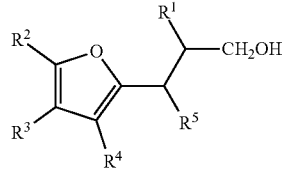

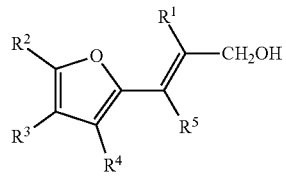

If the double bond is present, compound 10 may be the cis isomer, the trans isomer or a mixture of the cis and trans isomers with respect to the orientation of the furan and $R^1$ about the double bond. That is, compounds 10-a, 10-c and 10-f may be cis, trans, or a mixture thereof with respect to the furan and $R^1$.

The reaction may proceed in the presence of hydrogen and/or in the presence of a hydrogen donor. The hydrogen donor may be any suitable hydrogen donor, such as an alcohol, typically a $C_{1-25}$ or $C_{3-21}$ alcohol, and may be a primary or secondary alcohol. Additionally, mixture of alcohols may be used, such as 2, 3, 4 or more alcohols. In some embodiments, a secondary alcohol is used, such as a $C_{3-21}$ secondary alcohol or $C_{3-11}$ secondary alcohol. During the reaction, the alcohol moiety may be converted to a carbonyl moiety. One such exemplary embodiment is shown in Scheme 3.

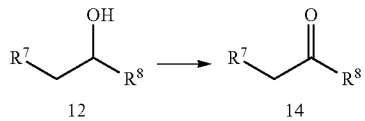

With respect to Scheme 3, each of $R^7$ and $R^8$ independently is H or alkyl such that $R^7$ and $R^8$, together with the carbon atoms to which they are attached, forms a $C_{2-25}$ carbon chain. In some embodiments, alcohol 12 is a primary alcohol where $R^8$ is H, but in other embodiments, alcohol 12 is a secondary alcohol and $R^8$ is not H. In certain embodiments, $R^7$ and $R^8$, together with the carbon atoms to which they are attached, forms a $C_{3-21}$ secondary alcohol, such as a $C_{3-11}$ secondary alcohol, and in particular embodiments, $R^8$ is $CH_3$ and $R^7$ is H or $C_{1-18}$ alkyl, such as $C_{1-8}$ alkyl. Exemplary alcohols that are useful in the reaction include, but are not limited to, 2-propanol, 2-butanol, 2-pentanol, 2-hexanol, 2-heptanol or any mixture thereof. And in some embodiments of scheme 2, an excess of alcohol 12 is used, such as a molar ratio of alcohol to compound 6 of from 10:1 to 1000:1.

Additionally, the reaction may proceed in the presence of a catalyst. The catalyst may be a single catalyst or it may be a mixture of catalysts. The catalyst may comprise a metallic catalyst, a metal oxide, or a mixture thereof. The metal oxide may comprise a single metal, or multiple metals, such as 2, 3, 4, or more metals, in addition to oxygen. And the metallic catalyst may comprise a single metal or a mixture of metals, such as 2, 3, 4, or more metals. Typically, the metallic catalyst is provided on a support substrate. Suitable support substrates include any substrate that facilitates the metallic catalyst functioning as a catalyst in the reaction. In some embodiments, the support substrate is carbon, but in other embodiments, the support substrate is, or comprises, a metal oxide. The metal oxide may be the same metal oxide that is included in the catalyst, or it may be a different metal oxide, such as a non-catalytic metal oxide. Metals suitable for use as in the metallic catalyst include, but are not limited to, Re, Ni, Cu, Pd, Ru, Rh, Pt, Ag, Au, Ir, Zn or mixtures thereof. Elements suitable for use as oxides include but are not limited to Cu, Pd, Ru, Ir, Ti, Sn, Mo, Fe, In, W, Ni, Co, Zn, V. In some embodiments comprising both a metallic catalyst and a metal oxide, the metal(s) in the metallic catalyst and the metal oxide may be the same, or they may be different. In certain disclosed embodiments, the catalyst is, or comprises, Ru/C, $RuO_2 \cdot H_2O$, $In_2O_3$, or a combination thereof.

Suitable temperatures for the reaction include any temperature that facilitates the formation of the desired products. In some embodiments, the reaction is heated at a temperature of 120° C. or less to 240° C. or more, such as 120° C. to 220° C., of from 150° C. to 220° C., or from 150° C. to 200° C. Additionally, or alternatively, the reaction may proceed at a suitable pressure, such as an ambient pressure or an autogenous pressure where the reaction proceeds in a sealed reaction vessel and the pressure increases inside the vessel as the reaction temperature increases. The reaction may be heated for from greater than zero to 48 hours or more, such as from 1 hour to 48 hours, from 4 hours to 42 hours, from 4 hours to 36 hours, or from 6 hours to 24 hours.

In some embodiments, the reaction temperature, pressure, reaction time and/or catalyst may be selected to facilitate formation of desired compounds according to one or more, such as 1, 2, 3, 4, 5 or 6, of formulas 10-a, 10-b, 10-c, 10-d, 10-e and/or 10-f.

After heating, the oleofuran product(s) may be isolated by techniques known to persons of ordinary skill in the art. For example, the catalyst may be removed by any suitable technique, such as filtration or decanting, and the resulting liquid may be heated to distill of at least a portion, or substantially all, of the solvent, unreacted starting materials such as excess alcohol, and/or unwanted reaction products such as compound 14. Typically, for detergent production, compound 10 is left as a mixture of oleofuran compounds that is not further purified.

III. Examples

Example 1

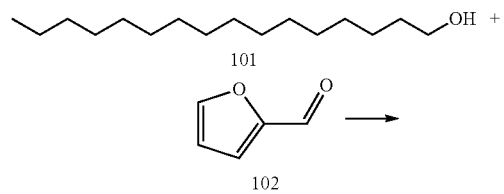

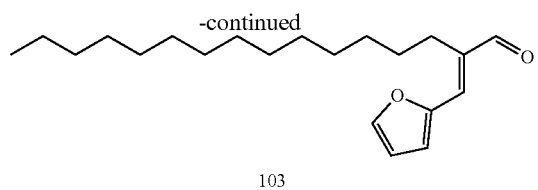

1 mmol of hexadecanol 101, a fatty alcohol, was combined with 2 mmol of furfural 102 in toluene solvent (1.5 mL) and mixed with 200 mg HT in a batch reactor. The mixture was heated at 150° C. under autogenous pressure for 20 hours resulting in compound 103 in a 75% yield.

Example 2

1 mmol of hexadecanol 101, 3 mmol of furfural 102, 1 mmol of triethylamine, and 0.05 mmol of nickel (II) acetylacetonate were mixed in a batch reactor. The mixture was heated at 180° C. under autogenous pressure for 20 hours. The reaction resulted in 90% yield of adduct 103.

Example 3

Four batch reactors were charged with 1 mmol of hexadecanol 101, 2 mmol of furfural 102 in cyclohexane solvent (1.5 mL) and 200 mg HT catalyst. The reactors were heated at 150° C. under autogenous pressure for 20 hours. The solids were separated from the reaction mixtures and the resulting liquids were combined. 0.5 mL of the combined liquid was mixed with 2.5 mL of 2-pentanol, 40 mg of Ru/C and 40 mg $RuO_2 \cdot H_2O$. The mixture was heated at 180° C. under autogenous pressure for 22 hours. The reaction yielded 98% of compound 103, followed by 25% yield of products 104-107, with compounds 104 and 105 being the major products.

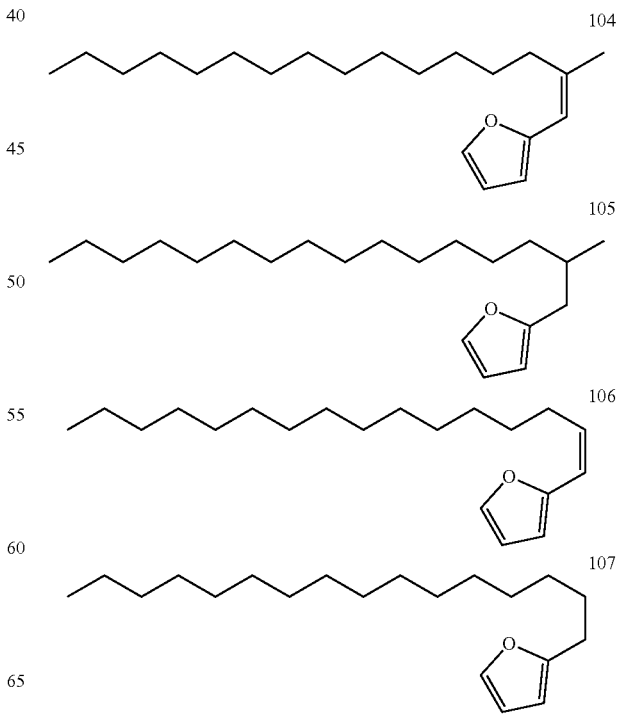

-continued

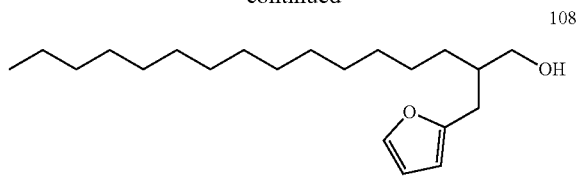

108

Example 4

Four batch reactors were charged with 1 mmol of hexadecanol 101, 2 mmol of furfural 102 in cyclohexane solvent (1.5 mL) and 200 mg HT catalyst. The reactors were heated at 150° C. under autogenous pressure for 20 hours. The solids were separated from the reaction mixtures and the resulting liquids were combined. 0.5 mL of the combined liquid was mixed with 2.5 mL of 2-pentanol, 20 mg of $Pd/SiO_2$ and 40 mg $RuO_2.H_2O$. The mixture was heated at 180° C. under autogenous pressure for 22 hours. The reaction yielded 75% of compound 103, followed by 15% yield of products 104-107, with compounds 106 and 107 being the major products.

Example 5

Four batch reactors were charged with 1 mmol of hexadecanol 101, 2 mmol of furfural 102 in cyclohexane solvent (1.25 mL) and 200 mg HT catalyst. The reactors were heated at 150° C. under autogenous pressure for 20 hours. The solids were separated from the reaction mixtures and the resulting liquids were combined. 0.5 mL of the combined liquid was mixed with 2.5 mL of 2-pentanol, 40 mg of Ru/C and 40 mg $RuO_2.H_2O$. The mixture was heated at 200° C. under autogenous pressure for 6 hours. The reaction yielded 79% of compound 103, followed by 97.8% yield of products 104-107, with compounds 104 and 105 being the major products.

Example 6

Four batch reactors were charged with 1 mmol of hexadecanol 101, 2 mmol of furfural 102 in cyclohexane solvent (1.25 mL) and 200 mg HT catalyst. The reactors were heated at 150° C. under autogenous pressure for 20 hours. The solids were separated from the reaction mixtures and the resulting liquids were combined. 0.5 mL of the combined liquid was mixed with 2.5 mL of 2-pentanol, 40 mg of Ru/C and 200 mg $In_2O_3$. The mixture was heated at 200° C. under autogenous pressure for 20 hours. The reaction yielded 76% of compound 103, followed by 49.4% yield of products 104-108, with compounds 104, 105 (17.9% sum) and 108 (25.7% sum) being the major products.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A method, comprising:
forming a first mixture comprising a fatty alcohol and a compound according to formula 1 in the presence of a first catalyst

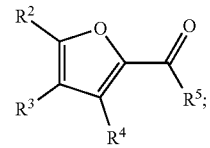

Formula 1 heating the first mixture at a first temperature of from 100° C. to 200° C. to form a compound according to formula 2

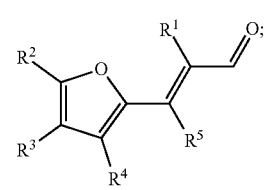

Formula 2 and
heating the compound according to formula 2 at a second temperature of from 120° C. to 240° C. in the presence of hydrogen and a second catalyst to form one or more compounds according to formula 3

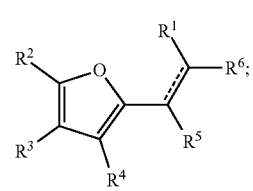

Formula 3 wherein
$R^1$ is aliphatic;
each of $R^2$, $R^3$, and $R^4$ independently is H, aliphatic, aldehyde, or OH;
$R^5$ is H or alkyl;
$R^6$ is H, $CH_3$ or $CH_2OH$; and
--- indicates that a bond may be a single bond or a double bond.

2. The method of claim 1, wherein the fatty alcohol has a formula

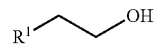

wherein $R^1$ is as defined for Formulas 1-3 in claim 1.

3. The method of claim 1, wherein:
$R^1$ is alkyl;
each of $R^2$, $R^3$, and $R^4$ independently is H or $C_{1-6}$alkyl;
$R^5$ is H or $C_{1-3}$alkyl;
or a combination thereof.

4. The method of claim 3, wherein:
$R^2$, $R^3$, and $R^4$ are all H;
$R^5$ is H;
or a combination thereof.

5. The method of claim 1, wherein the first catalyst is a basic catalyst.

6. The method of claim 1, wherein:
the first catalyst comprises magnesium oxide;
the first catalyst is a mixed oxide catalyst comprise magnesium and aluminum; or
the first catalyst is a nickel catalyst.

7. The method of claim 1, wherein the first catalyst is a homogeneous Ni(II) catalyst.

8. The method of claim 1, wherein the first catalyst is nickel (II) acetylacetonate.

9. The method of claim 1, wherein forming the first mixture comprises forming the first mixture in the presence of a base.

10. The method of claim 9, wherein the base is an organic base, inorganic base, or a combination thereof.

11. The method of claim 1, wherein heating the compound according to formula 2 in the presence of hydrogen comprises heating the compound according to formula 2 in the presence of hydrogen gas or a hydrogen donor.

12. The method of claim 11, wherein the hydrogen donor is an alcohol.

13. The method of claim 12, wherein the alcohol is a secondary alcohol.

14. The method of claim 12, wherein the alcohol is 2-propanol, 2-butanol, 2-pentanol, 2-hexanol, 2-heptanol or a combination thereof.

15. The method of claim 1, wherein the second catalyst is a metal oxide, a metallic catalyst, or a combination thereof.

16. The method of claim 15, wherein the second catalyst comprises an oxide of Cu, Pd, Ru, Ir, Ti, Sn, Mo, Fe, In, W, Ni, Co, Zn, V or a combination thereof.

17. The method of claim 15, wherein the metallic catalyst comprises Re, Ni, Cu, Pd, Ru, Rh, Pt, Ag, Au, Ir, Zn or mixtures thereof.

18. The method of claim 1, wherein the second catalyst comprises Ru/C, $RuO_2 \cdot H_2O$, $In_2O_3$, or a combination thereof.

19. The method of claim 1, wherein the one or more compounds according to formula 3 are selected from

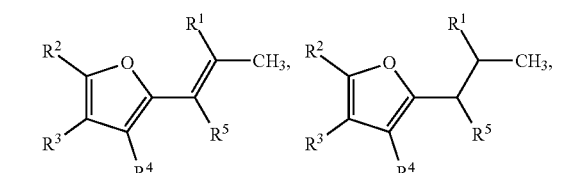

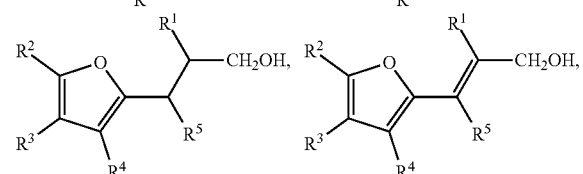

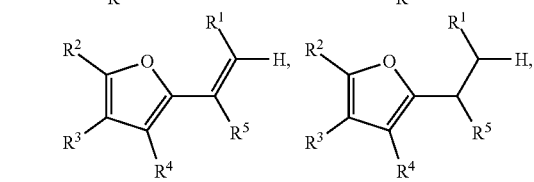

or a combination thereof.

20. A method, comprising:
forming a first mixture comprising an alcohol having a formula

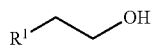

and a compound according to formula 1 in the presence of a first catalyst comprising magnesium and aluminum oxides

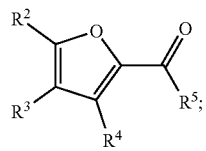

Formula 1 heating the first mixture at a first temperature of from 130° C. to 170° C. to form a compound according to formula 2

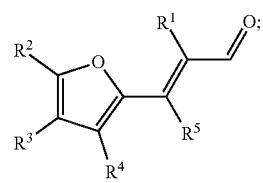

Formula 2 and
heating the compound according to formula 2 at a second temperature of from 150° C. to 220° C. in the presence of a secondary alcohol having a formula

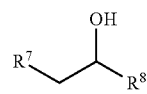

and a second catalyst comprising a metallic catalyst and a metal oxide to form one or more compounds according to formula 3

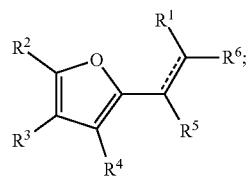

Formula 3 wherein
$R^1$ is $C_{2-22}$alkyl;
each of $R^2$, $R^3$, and $R^4$ independently is H or $C_{1-6}$alkyl;
$R^5$ is H;
$R^6$ is H, $CH_3$ or $CH_2OH$;
$R^7$ is H or $C_{1-18}$ alkyl;
$R^8$ is $CH_3$; and
=== indicates that a bond may be a single bond or a double bond.

* * * * *